United States Patent
Ten Hoeve et al.

(10) Patent No.: US 7,361,716 B2
(45) Date of Patent: Apr. 22, 2008

(54) METHOD OF PREPARING A POLYMER, METHOD OF PREPARING A COMPOUNDS, COMPOUNDS, POLYMERS, AND METHOD OF MANUFACTURING AN ELECTRONIC DEVICE

(75) Inventors: Wolter Ten Hoeve, Assen (NL); Margaretha Maria De Kok, Eindhoven (NL); Bart-Hendrik Huisman, Eindhoven (NL); Peter Tobias Herwig, Eindhoven (NL); Albert Jos Jan Marie Van Breemen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 714 days.

(21) Appl. No.: 10/048,040

(22) PCT Filed: May 25, 2001

(86) PCT No.: PCT/EP01/06049

§ 371 (c)(1),
(2), (4) Date: Jan. 24, 2002

(87) PCT Pub. No.: WO01/92369

PCT Pub. Date: Dec. 6, 2001

(65) Prior Publication Data

US 2003/0027963 A1    Feb. 6, 2003

(30) Foreign Application Priority Data

May 30, 2000    (EP) .................................. 00201911

(51) Int. Cl.
*C08L 65/00*    (2006.01)
*C08G 18/83*    (2006.01)

(52) U.S. Cl. ..................... 525/535; 525/410; 525/417; 528/374

(58) Field of Classification Search ................ 526/286; 525/410, 535, 417; 528/374
See application file for complete search history.

(56) References Cited

U.S. PATENT DOCUMENTS 4,766,198 A    8/1988    Harper et al.

4,900,782 A *    2/1990    Han et al. .................... 525/398
5,053,166 A    10/1991    Murase et al.

FOREIGN PATENT DOCUMENTS

| EP | 0705857 | 1/2000 |
|----|---------|--------|
| WO | WO 00/35987 | 6/2000 |
| WO | WO 01/18090 A1 | 3/2001 |
| WO | PCT/EP 01/06049 | 9/2001 |

OTHER PUBLICATIONS

Van Breeman et al., Highly Selective Route for Producing Unsymmetrically Substituted Monomers Toward Synthesis of Conjugated Polymers Derived from Poly(p-phenylene vinylene), 1999, pp. 3106-3112.

Cheng et al., "New Precursors and Plymerization Route for the Preparation of High Molecular Mass Poly (3,4-Dialkoxy-2,5-Thienylenevinylene)s: Low Band Gap Conductive Polymers", 1995, pp. 1451-1452.

"Polymerization of alpha, alpha' -Bis(dialkylsulfonio)-p-xylene Dihalids via p-Xylylene Intermediates: Evidence for a Nonradical Mechanism", 1988, pp. 7258-7259.

* cited by examiner

*Primary Examiner*—Fred Teskin
(74) *Attorney, Agent, or Firm*—Larry Liberchuk

(57) ABSTRACT

A polymer comprising structural units of the formula I is prepared according to a novel method, in which the starting compound $R_1$ 'S—$(CHR'_2)$—Ar—$(CHR_2)$—$SR_1$ is polymerized with a base, preferably in an aprotic solvent. The polymer comprises 50 to 1000 structural units of the formula I. The solution comprising the polymer thus prepared has a lower viscosity than a solution of a similar polymer with a greater chain length. The solution comprising the polymer thus prepared may be applied as a layer on a substrate. Electronic components with layers prepared with the polymer of the invention show better properties.

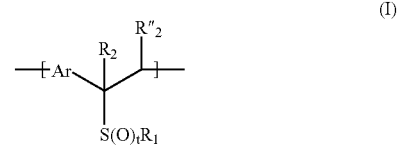

(I)

4 Claims, 1 Drawing Sheet

METHOD OF PREPARING A POLYMER, METHOD OF PREPARING A COMPOUNDS, COMPOUNDS, POLYMERS, AND METHOD OF MANUFACTURING AN ELECTRONIC DEVICE

Method of preparing a polymer, method of preparing a compound, compounds, polymers, and method of manufacturing an electronic device The invention relates to a method of preparing a polymer which comprises structural units of formula I,

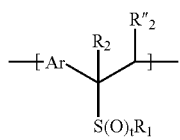

in which formula:
Ar is an aromatic cyclic system with 4 to 20 carbon atoms, which may be substituted with a substituent chosen from among a non-branched $C_1$-$C_{20}$-alkyl, $C_3$-$C_{20}$-alkoxy, $C_1$-$C_{20}$-alkylsulfate, a branched $C_3$-$C_{20}$-alkyl, phenyl or benzyl group and which may comprise up to 4 heteroatoms chosen from the group comprising oxygen, sulfur, and nitrogen in the aromatic cyclic system,
t is equal to 0, 1, or 2,
$R_1$ is chosen from the group comprising a non-branched $C_1$-$C_{20}$-alkyl group, a branched $C_3$-$C_{20}$ alkyl group, a cyclic $C_4$-$C_{20}$-alkyl group, a $C_1$-$C_4$-alkyl-substituted cyclic $C_4$-$C_{20}$-alkyl group, a phenyl group and a benzyl group, which groups may comprise heteroatoms,
$R_2$ and $R''_2$ are chosen from the group comprising a hydrogen atom and a $C_1$-$C_{20}$-alkyl and $C_4$-$C_{20}$-aryl group, which groups may comprise substituents.

The invention also relates to a method of preparing compounds having the formula II

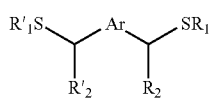

in which formula:
Ar is an aromatic cyclic system with 4 to 20 carbon atoms, which may be substituted with a substituent chosen from among a non-branched $C_1$-$C_{20}$-alkyl, $C_3$-$C_{20}$-alkoxy, $C_1$-$C_{20}$-alkylsulfate, a branched $C_3$-$C_{20}$-alkyl, phenyl or benzyl group and which may comprise up to 4 heteroatoms chosen from the group comprising oxygen, sulfur, and nitrogen in the aromatic cyclic system,
$R_1$ and $R_1'$ are chosen from the group comprising a non-branched $C_1$-$C_{20}$-alkyl group, a branched $C_3$-$C_{20}$ alkyl group, a cyclic alkyl group, a $C_1$-$C_4$-alkyl-substituted cyclic alkyl group, a $C_4$-$C_{14}$-aryl group, and a benzyl group, which groups may comprise heteroatoms,
$R_2$ and $R_2'$ are chosen from the group comprising a hydrogen atom and a $C_1$-$C_{20}$-alkyl and a $C_4$-$C_{20}$-aryl group, which groups may comprise substituents.

The invention also relates to compounds and polymers.
The invention further relates to a composition of polymers.

The invention further relates to a method of preparing a polymer with structural units having the formula VI,

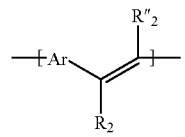

in which Formula:
Ar is an aromatic cyclic system with 4 to 20 carbon atoms, which may be substituted with a substituent chosen from among a non-branched $C_1$-$C_{20}$-alkyl, $C_3$-$C_{20}$-alkoxy, $C_1$-$C_{20}$-alkylsulfate, a branched $C_3$-$C_{20}$-alkyl, phenyl or benzyl group and which may comprise up to 4 heteroatoms chosen from the group comprising oxygen, sulfur, and nitrogen in the aromatic cyclic system, and
$R_2$ and $R''_2$ are chosen from the group comprising a hydrogen atom and a $C_1$-$C_{20}$-alkyl and $C_4$-$C_{20}$-aryl group, which groups may comprise substituents.

The invention further relates to a method of manufacturing a layer of a polymer with structural units having the formula VI,

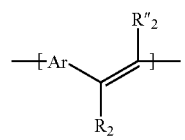

in which formula:
Ar is an aromatic cyclic system with 4 to 20 carbon atoms, which may be substituted with a substituent chosen from among a non-branched $C_1$-$C_{20}$ -alkyl, $C_3$-$C_{20}$-alkoxy, $C_1$-$C_{20}$-alkylsulfate, a branched $C_3$-$C_{20}$-alkyl, phenyl or benzyl group and which may comprise up to 4 heteroatoms chosen from the group comprising oxygen, sulfur, and nitrogen in the aromatic cyclic system, and
$R_2$ and $R''_2$ are chosen from the group comprising a hydrogen atom and a $C_1$-$C_{20}$-alkyl and $C_4$-$C_{20}$-aryl group, which groups may comprise substituents, which method comprises
the application of a solution of the polymer comprising structural units having the formula I as a layer on a substrate,

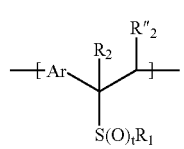

in which formula I:
t is equal to 0, 1 or 2,
$R_1$ is chosen from the group comprising a non-branched $C_1$-$C_{20}$-alkyl group, a branched $C_3$-$C_{20}$ alkyl group, a cyclic $C_4$-$C_{20}$-alkyl group, a $C_1$-$C_4$-alkyl-substituted cyclic $C_4$-$C_{20}$-alkyl group, a phenyl group, and a benzy group, which groups may comprise heteroatoms, and $R_2$, $R''_2$, and Ar are equal to $R_2$, $R''_2$ and Ar in formula VI, and the conversion through heating of the polymer comprising structural units of the formula I into the polymer comprising structural units of the formula VI.

The invention further relates to an electronic device comprising a layer of a polymer with mainly the structural units having the formula VI:

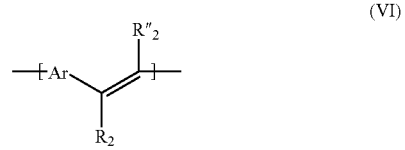

in which formula:

Ar is an aromatic cyclic system with 4 to 20 carbon atoms, which may be substituted with a substituent chosen from among a non-branched $C_1$-$C_{20}$-alkyl, $C_3$-$C_{20}$-alkoxy, $C_1$-$C_{20}$-alkylsulfate, a branched $C_3$-$C_{20}$-alkyl, phenyl or benzyl group and which may comprise up to 4 heteroatoms chosen from the group comprising oxygen, sulfur, and nitrogen in the aromatic cyclic system, and $R_2$ and $R''_2$ are chosen from the group comprising a hydrogen atom and a $C_1$-$C_{20}$-alkyl and $C_4$-$C_{20}$-aryl group, which groups may comprise substituents.

Such a method of preparing a polymer is known from EP-B 705857. In the known method, the polymer is prepared from a compound having the formula X:

in which formula Y and Y' each represent a leaving group such as Cl, Br, F, tosylate.

A reaction of the compound with formula X with a thiole $R_1SH$ yields a non-symmetrical intermediate product, a compound in accordance with the formula X in which Y' is equal to $SR_1$. Purification then takes place by means of column chromatography, followed by oxidation and polymerization of this intermediate product into the polymer with structural units having the formula I. This polymer may be provided as a layer on a substrate, whereupon the group $S(O)_tR_1$ is eliminated.

A disadvantage of the known method of preparing a polymer is that the purification step by means of column chromatography is time-consuming and difficult to industrialize. A disadvantage of the known method of preparing a compound of the formula II is that usually the toxic HCl gas is used for preparing the basic ingredient. A disadvantage of the known method of preparing a compound with structural units according to the formula VI, e.g. the elimination of the $S(O)_tR_1$-group from the polymer having structural units of the formula I, is that $S(O)_tR_1$-groups with t unequal to 1 are eliminated at higher temperatures or not at all. A disadvantage of the known method of manufacturing a layer is that the solution of the polymer having structural units of the formula I has a high viscosity, i.e. of approximately 100× $10^{-3}$ Pa·s. Filtering of the solution and the process of providing the layer on the substrate are sluggish processes owing to the high viscosity.

It is a first object of the invention to provide a method of preparing a polymer of the kind mentioned in the opening paragraph which can be readily implemented on an industrial scale.

It is a second object of the invention to provide a method of preparing a compound of the kind mentioned in the opening paragraphs wherein no toxic gases are used for the conversion of H—Ar—H into the basic ingredient.

It is a third object of the invention to provide a method of preparing a polymer having structural units of the formula I, as mentioned in the opening paragraphs, which results in a polymer with a chain conjugation that is substantially larger.

It is a fourth object of the invention to provide a method of manufacturing a layer of the kind mentioned in the opening paragraphs which is not hampered by the viscosity.

It is a fifth object of the invention to provide an electronic device of the kind mentioned in the opening paragraphs which has improved properties.

The first object is realized in that the method starts with a compound having the formula II

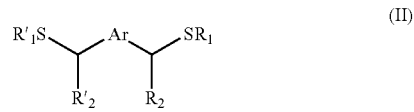

in which formula $R'_1$ is chosen from the group comprising a non-branched $C_1$-$C_{20}$-alkyl group, a branched $C_3$-$C_{20}$ alkyl group, a cyclic alkyl group, a $C_1$-$C_4$-alkyl-substituted cyclic alkyl group, a phenyl and a benzyl group, which groups may comprise heteroatoms, $R_1$, $R_2$, and Ar are equal to $R_1$, $R_2$, and Ar in formula I, and $R'_2$ is chosen from the group comprising a hydrogen atom and a $C_1$-$C_{20}$-alkyl and $C_4$-$C_{20}$-aryl group, which groups may comprise substituents, and that the polymer with structural units of the formula I is converted through polymerization with the aid of a base into a polymer which comprises units having the formula III

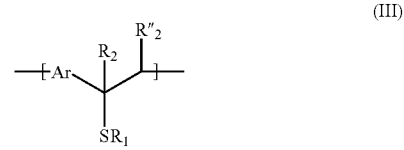

in which formula $R_1$, $R_2$, and Ar are equal to $R_1$, $R_2$, and Ar in formula II, and $R'_2$ is chosen from the group comprising $R_2$ and $R'_2$, and through oxidation of at least a number of the units of the polymer having the formula III for the preparation of the polymer with units having the formula I, in which formula t is equal to 1 or 2.

The monomer in the method according to the invention—the compound having the formula II—has a thioalkyl group $R_1S$, $R'_1S$ on either side prior to the polymerization step. This is advantageous because no purification step is now necessary for obtaining the compound having the formula II in a substantially pure form. The monomer is created by means of at least two molar equivalents of thiole to one molar equivalent of the basic substance—the compound having the formula X—instead of a non-symmetrical compound which has a thioalkyl group at one side of the Ar group only. An additional advantage is that the monomer may in principle also be prepared from other basic substances than the compound having the formula X, which can be prepared with hazardous chemicals only, such as a compound H—Ar—H.

It is surprising that the polymerization step can be carried out from the compound having the formula II in the method according to the invention. First of all, it appears to be essential that the polymerization step is carried out in alkaline conditions, at least one molar equivalent of a base being used.

It is furthermore surprising that the polymer formed with structural units having the formula III has good properties. The inventors were able to prepare said polymer with a small chain length of between 50 and 1000 units. Contrarily, a chain length of 1800 to 7000 units was achieved in the prior-art method cited above. The chain length was determined in an analysis of GPC with polystyrene as the standard, which is a usual method of analysis.

In addition, the polymer thus obtained is a substantially linear polymer, i.e. no branching-off of the chain of the polymer and no cross-linking of different polymer chains occur during the polymerization. The linearity of the polymer formed is important for the processing; polymers with strongly branched and cross-linked chains can be provided as layers on substrates with difficulty only. The linearity is furthermore important for the structure of a layer of a polymer with structural units having the formula I. An increasing linearity of a polymer chain with structural units having the formula I increases the probability that a certain orderly arrangement will arise in the layer at least locally. Such an orderly arrangement would seem to be favorable, for example, for the electrical characteristics of the polymer. Furthermore, the polymer prepared by the method according to the invention shows fewer defects in the polymer chain than a polymer prepared by the prior-art method. The presence of defects is in fact no longer detectable by means of NMR, which means that the defect rate is below 1%. The smaller number of defects implies that the polymer resulting after elimination of the $S(O)_pR_1$ groups has a chain which is conjugated over a greater length: the chain has a greater conjugation length. It is suspected that this microscopic property manifests itself in a higher mobility and a higher electroluminescence.

In addition, the small number of defects offers the possibility of influencing the conjugation length. This influence may be exerted, for example, in that the $S(O)_pR_1$ groups in the polymer are oxidized after polymerization such that p is equal to 1 for a portion of the groups and p is equal 2 for another portion. Since the elimination of the $SOR_1$ and $SO_2R_1$ groups takes place at different temperatures, a polymer may be formed which still comprises $SO_2R_1$ groups and accordingly has a shorter conjugation length.

It is an advantage of the method according to the invention that the group $R_1$ may be chosen from a wider range of groups. This variability is limited to a lesser extent by synthetic problems than is the variability of groups in the prior-art method.

Precursor polymers with the formula VI which can be prepared by the method preferably comprise as the—Ar group an aromatic group chosen from among 1,4-phenylene, 2,6-naphthalenediyl, 1,4-naphthalenediyl, 1,4 anthracenediyl, 2,6-anthracenediyl, 9,10-anthracenediyl, 2,5-thienylene, 2,5-furanediyl, 2,5-pyrrolediyl, 1,3,4-oxadiazole-2,5-diyl, 1,3,4-thiadiazole-2,5-diyl, 2,5-benzo[c]-furanediyl, 2,5-benzo[c]-pyrrolediyl, 2,5-benzo[c]thienylene, thieno[3,2-b]thiophene-2,5-diyl, pyrrolo[3,2-b]pyrrole-2,5-diyl, pyrene-2,7-diyl, 4,5,9,10-tetrahydropyrene-2,7-diyl, 4,4'-biphenylene, phenantrene-2,7-diyl, 9,10-dihydrophenantrene-2,7-diyl, dibenzofurane-2,7-diyl, dibenzothiophene-2,7-diyl, carbazole-2,7-diyl, of which the nitrogen-containing groups may be substituted on the nitrogen atom with a $C_1$-$C_{22}$-alkyl or a $C_2$-$C_{10}$-aryl group, while in all said groups R atoms on the aromatic rings may be substituted by a $C_1$-$C_{22}$ linear or branched alkyl group, $C_4$-$C_{14}$-aryl group, electron-donating groups such as $C_1$-$C_{22}$ linear or branched alkoxy and alkylthio groups, and halogen atoms or electron-absorbing groups such as cyano, nitro, and ester groups, while the $C_1$-$C_{14}$-aryl group itself may be substituted by electron-donating or electron-absorbing groups.

In general, metal bases, ammonium bases, and uncharged bases may be used ,I as the base. Examples of uncharged bases include triethyl amine, pyridine and noninore phosphazene bases like 1-tert-butyl-4,4,4-tris(dirneth ylarino)-2,2-bis[tris(dimethylamino)-phosphoranylidenamino]-2 $\lambda^5$, 4 $\lambda^5$-catenadi(phosphazene), 1-tert-butyl-2,2,4,4,4-pentakis(dimethylaniino)-2,2-bis[tris(dimethylamino)-phosphoranylidenamino]-2 $\lambda^5$, 4 $\lambda^5$-catenadi(phosphazene) and tert-butylimino-tris(dimcthylamino)phosphorane. Examples of metal and ammonium bases are metal hydrides such as NaH, KH, metal hydroxides such as NaOH, LiOH, KOH, metal alkoxides such as NaOMe, NaOEt, KOtBu, metal amides such as $NaNH_2$, $NaN(SiMe_3)_2$, lithium diisopropylamide, organometallic compounds such as n-butyllithium, Grignard reagentia, and substituted ammonium hydroxides.

Preferably, an aprotic solvent is used. There is a risk with protic solvents that the base deprotonizes the solvent. It is found that this weakening of the base adversely affects the polymerization. Instead of a single solvent, a mixture of solvents may alternatively be used. Examples of classes of solvents are amides, amines, sulfons, sulfoxides, polyethers, cyclic ethers, and unsaturated ethers. Examples of advantageous solvents are inter alia Imonomethylformamide, dimethylformamide, imidazolidone, pyrrolidone, dimethylsulfoxide, dichloromethane, sulfolane, sulfolene, 1,3-diihethylimidazolidine-2-one, tetrahydrofurane, triethyleneglycol.

If the polymer comprising units having the formula I is desired in which t is equal to 1 or 2, the polymer with units having the formula III is at least partly oxidized. It is found that an elimination of the $S(O)_tR_1$ group with t equal to 1 or 2 takes place at a lower temperature than an elimination of the $SR_1$ group. It is important that the elimination temperature should be low, preferably lower than 300° C., especially in the manufacture of devices which comprise one or several layers of an organic material in addition to the layer of the polymer having structural units of the formula I.

In an embodiment, the —Ar— unit chosen is the unit having the formula IV

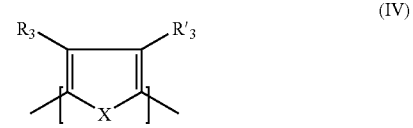

(IV)

in which formula

X is chosen from the group of O, S, $NR_6$, $R_3$ and $R'_3$ may be identical and are chosen from the group comprising hydrogen, a chlorine, a bromine, a fluorine, and an iodine atom, a $C_1$-$C_4$-alkyl, a carbonitryl, tnhalomethyl, hydroxy, nitro, amino, carboxyl, sulfoxyl, sulfonate and carbonate group, and a substituted and non-substituted phenyl, alkylaryl, and arylalkyl, alkoxy, and thioalkoxy group, and $R_6$ is chosen from the group comprising a hydrogen atom and $C_1$-$C_{20}$ alkyl, aryl, $C_1$-$C_{20}$-alkylaryl, and arylalkyl group.

In this embodiment, the polymer with structural units having the formula I is a precursor polymer of polythienylene-vinylene, which polythienylene-vinylene is also referred to as PTV. PTV has semiconducting properties, which is why the material is used inter alia as a p-type semiconductor layer in a transistor. An advantage of PTV over other semiconductors is its easy processability. A layer of the readily soluble precursor polymer may be provided by a coating technique, whereupon elimination to PTV is easy. The layer of PTV is not attacked if this layer is used as a substrate for a subsequent layer of a different material.

In an alternative embodiment, the —Ar— unit chosen is the unit having the formula V

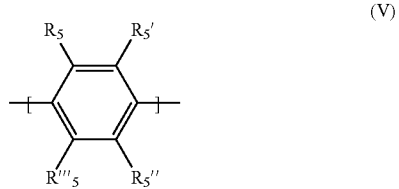

in which formula $R_5$, $R'_5$, $R''_5$, and $R'''_5$ may be identical and are chosen from the group comprising a hydrogen, chlorine, bromine, fluorine, and iodine atom, and $C_1$-$C_{22}$-alkyl, carbonitryl, trihalomethyl, hydroxy, nitro, amino, carboxyl, sulfoxyl, sulfonate, and carbonate group, and an optionally substituted phenyl, $C_1$-$C_{22}$-alkylaryl and arylalkyl, $C_1$-$C_{22}$-alkoxy, and $C_1$-$C_{22}$thioalkoxy group.

In this embodiment, the polymer with structural units having the formula I is a precursor polymer of polyparaphenylene-vinylene, which potyparaphernylene-vinylene is also referred to as PPV. PPV is highly suitable for use as an electroluminescent material for use in a light-emitting diode which consists at least partly of polymeric material. Advantageous examples of PPV and PPV precursors have as their $R_5$ group a phenyl group or a 3,7-dimethyloctyl-1-oxy group. The unit of a phenyl-substituted PPV is a 2,5-bis(1, 1'-biphenyl). In contrast to the 1,1 '-bis(4,4'-biphenyl), the aromatic system of a unit of the polymeric chain in the phenyl-substituted PPV is limited to a single phenylene group.

The second object is achieved in the method of preparing a compound having the formula II, in that H—Ar—H reacts with $R_1$SH and $R_2$—(C═O)—H and with $R'_1$SH and $R'_2$-(C═O)—H so as to form the compound having the formula II.

It was surprisingly found that the compound having the formula II can be directly prepared from H—Ar—H, a thiole $R_1$SH, and an aldehyde $R_2$—(C═O)—H without a synthesis of the compound having the formula X being necessary. Preparation takes place in an acidic solution, which has the advantage that no polymerization takes place in principle during preparation. Aldehydes $R_2$—(C═O)—H and $R'_2$—(C═O)—H which are used, for example, are acetaldehyde, benzaldehyde, or p-formaldehyde. $R_2$ and $R'_2$ may be different, but preferably they are the same. Preferably, thiophenol or alkylmercaptane is chosen for $R_1$SH and $R'_1$SH. $R_1$ and $R'_1$ may be different, but preferably they are the same. Favorable examples of H—Ar—H are thiophene and dialkoxybenzene. Examples of acids in the acidic solution are hydrochloric acid and hydrobromic acid.

It is an advantage of the method that substituents can be readily introduced into the polymer in a simple manner through variation of the groups $R_2$ and $R'_2$. These substituents are present not only in the polymer with structural units having the formula I, but also in the polymer arising therefrom through elimination of the $S(O)_rR_1$ group and having electroluminescent or semiconducting properties. The properties of said polymers can be adjusted by means of the substituents.

Furthermore, compounds having the formula II were prepared, in which formula

Ar is an aromatic cyclic system with 4 to 20 carbon atoms, which may be substituted with a substituent chosen from the group comprising a non-branched $C_1$-$C_{20}$-alkyl, $C_3$-$C_{20}$-alkoxy, $C_1$-$C_{20}$-alkylsulfate, a branched $C_3$-$C_{20}$-alkyl, phenyl or benzyl group, and which may comprise up to 4 heteroatoms chosen from the group comprising oxygen, sulfur, and nitrogen in the aromatic cyclic system, $R_1$ and $R'_1$ are chosen from the group comprising a non-branched $C_1$-$C_{20}$-alkyl group, a branched $C_3$-$C_{20}$-alkyl group, a cyclic alkyl group, a $C_1$-$C_4$-alkyl-substituted cyclic alkyl group, a $C_4$-$C_{14}$-aryl group, and a benzyl group, which groups may comprise heteroatoms, $R_2$ is chosen from the group comprising a $C_1$-$C_{20}$-alkyl and $C_4$-$C_{20}$-aryl group, which groups may comprise substituents, and $R'_2$ is chosen from the group comprising a hydrogen atom, a $C_1$-$C_{20}$-alkyl, and a $C_4$-$C_{20}$-aryl group, which groups may contain substituents.

In the compounds according to the invention, $R_2$ comprises an alkyl or aryl group. This group may be substituted with a substituent such as sulfate, sulfonic acid, hydroxide, cyanide, nitro, amino, carboxyl, and carbonyl. If $R_2$ and $R_2'$ are different and $R_1$ and $R_1'$ are different, stereo isomers and other isomers of the exemplary class of compounds having the formula II may be formed. The class of compounds having the formula II, however, should be interpreted such that it also includes the stereo isomers and other isomers.

Furthermore, polymers comprising structural units having the formula III were prepared. These polymers result from the method of formula I without an additional oxidation being carried out. It was found that the polymers comprising structural units having the formula II are stable in the air for at least a number of weeks, in contrast to polymers comprising structural units having the formula I with p equal to 1 or 2. The polymers comprising structural units having the formula III are thus favorable intermediate products which can be stored and transported without problems.

Furthermore, polymers comprising structural units having the formula I were prepared, which polymers have a chain length of at least 50 and at most 1000 units, in which formula I Ar is an aromatic system with 4 to 6 carbon atoms, which system may possibly be substituted and may contain a heteroatom. It is assumed that the mechanism for the formation of precursor polymers, for example comprising structural units having the formula I, proceeds via a true monomer formed in situ, probably a p-quinodimethane system. Polymerization of this true monomer seems to be self-initiated. The chain length of a formed polymer thus cannot be influenced by the reaction time or the quantity of initiator, but should be regarded as a material characteristic. The fact that the chain length of the polymer according to the invention is smaller than the chain length of the same polymer prepared by the prior-art method appears to be caused by a different behavior of the $SR_1'$ group with respect to Y, which is chosen from Cl, Br, F, and tosylate. This explanation is supported by an embodiment of the prior-art in which Y and Y' are equal to n-butylsulfinyl (n-$C_4H_9SO$). In this embodiment, the molar weight is 3800 g/mole, which corresponds to a chain length of approximately 19.

Furthermore, a composition of polymers with structural units having the formula IX was prepared

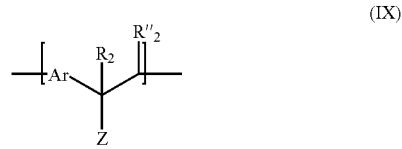

(IX)

in which:

Ar is an aromatic cyclic system with 4 to 20 carbon atoms, which may be substituted with a substituent chosen from among a non-branched $C_1$-$C_{20}$-alkyl, $C_3$-$C_{20}$-alkoxy, $C_1$-$C_{20}$-alkylsulfate, a branched $C_3$-$C_{20}$-alkyl, phenyl or benzyl group and which may comprise up to 4 heteroatoms chosen from the group comprising oxygen, sulfur, and nitrogen in the aromatic cyclic system, $R_2$ and $R''_2$ are chosen from the group comprising a hydrogen atom and a $C_1$-$C_{20}$-alkyl and $C_4$-$C_{20}$-aryl group, which groups may optionally comprise substituents, and Z is chosen from a group comprising $S(O)_pR_1$, $OR_2$, in which p is equal to 0, 1 or 2, and $R_1$ and $R_2$ are chosen from the group comprising a non-branched $C_1$-$C_{20}$-alkyl group, a branched $C_3$-$C_{20}$-alkyl group, a cyclic $C_4$-$C_{20}$-alkyl group, a $C_1$-$C_4$-alkyl-substituted cyclic $C_4$-$C_{20}$-alkyl group, a phenyl group, and a benzyl group, which groups may contain heteroatoms, wherein a first fraction of the composition comprises polymers with structural units having the formula IX with Z equal to $S(O)_pR_1$ and a chain length of 50 to 1000 units, and a second fraction of the composition comprises polymers with a chain length of more than 1000 units.

Solutions of precursor polymers prepared by different methods may be mixed in order to attune the viscosity to the envisaged application. The mixing possibility has the advantage that the viscosity of the solution can be adjusted as desired.

The third object of the invention is achieved in the method of preparing a conjugated polymer of the kind mentioned in the opening paragraphs in that a polymer comprising structural units of formula III is converted directly into the polymer comprising structural units of formula VI by heating under catalysis of acid. This direct conversion is in fact an elimination of the sulfide group $SR_1$. The inventors are of the opinion that the elimination of the $SR_1$-group occurs via a sulphonium-ion, as said sulphonium ion has an lower elimination temperature than the sulfide $SR_1$-group.

The method of preparing a conjugated polymer has important advantages about the two-step elimination method comprising the oxidation of the sulfide group to a sulfinyl-group—$SOR_1$. It was observed that the oxidation is very sensitive for the amount of oxidizer. While using more or less than one equivalent of oxidizer, a polymer with sulfonylgroups—$SO_2R_1$ or with sulfidegrpups—$SR_1$ next to sulfinylgroups—$SOR_1$ were obtained regularly. It further turned out that the—$SO_2R_1$ and the—$SR_1$—groups are less easily eliminated than the —$SOR_1$-group, and actually were not eliminated at all in many elimination experiments. The resulting polymers showed only a moderate electroluminescent efficiency and a somewhat nasty injection barrier, when applied in an electroluminescent device. Now having found a better elimination method, it appears that this moderate electroluminescent efficiency can be ascribed to the not eliminated—$SOR_1$—and—$SR_1$—group, which lead to an interruption of the conjugation in the conjugated polymer.

Experiments have shown, that the acid catalysed elimination of the—$SR_1$—group from the polymer comprising structural units of the formula III works in solution and after applying said precursor polymer as a layer onto a substrate. The amount of acid used can be as little as 5 mole %, of the amount of the precursor polymer which includes a large number of sulfide groups. This shows that the acid is a true catalyst.

The fourth object of the invention is achieved in the method of manufacturing a layer of the kind mentioned in the opening paragraphs in that the solution to be provided as a layer comprises a polymer with structural units having the formula I, with a chain length of at least 50 and at most 1000 units.

It was found that the solution of the precursor polymer with a chain length of between 50 and 1000 has a viscosity of approximately 5 to 15 mPa·s. This viscosity is approximately one order of magnitude smaller than the viscosity of the known solution of the precursor polymer with a chain length of more than 1000. This lower viscosity prevents the problem that the solution of the precursor polymer stays behind in devices such as spin coating machines and filters. In addition, steps such as filtration and spin coating may be carried out at a higher speed and at normal pressures and temperatures. The precursor polymer with a smaller chain length may be prepared by the preparation method according to the invention.

In an embodiment, the solution to be provided as a layer also comprises a polymer with structural units having the formula I and with a chain length of at least 1000 units. Solutions of precursor polymers prepared by different methods may be mixed so as to attune the viscosity to the envisaged application. The mixing possibility has the advantage that the viscosity of the solution can be adjusted as desired. The mixing possibility may be advantageous not only for the processing properties, but also for the properties of the layer. The chain length is found to influence, for example, the luminescence of a polymer arising after elimination of the $S(O)_pR_1$ group. The luminescence can accordingly be adjusted through mixing of solutions of precursor polymers of different chain lengths.

In an alternative embodiment, the method starts with a solution of a polymer with structural units having the formula I, in which p is equal to 0, and the polymer with structural units having the formula I, in which p is equal to 0, is oxidized with a peroxide prior to the application of the solution as a layer, whereupon a polymer with structural units having the formula I is created in which p is equal to 1 in at least a proportion of the units. It was found that the precursor polymer with p equal to 0 has a good stability. It is accordingly favorable in practice to start with the precursor polymer with p equal to 0 previously prepared. The oxidation into the precursor polymer with p equal to 1 is achieved with a peroxide, such as m-perbenzoic acid. If it is desired that the conjugated chain contains as few defects as possible, one molar equivalent of peroxide should be added in the oxidation for each structural unit of the chain. Elimination of the $SO_2R_1$ groups is found to take place at a higher temperature than the elimination of the $SOR_1$ groups. If the layer is provided on a substrate of polymeric material, it is highly preferable for p to be equal to 1; degradation of the substrate may occur in the case of heating of the substrate and the layer up to the elimination temperature of the $SO_2R_1$ group.

The fifth object of the invention is achieved in that the polymer is prepared from at least a polymer with structural units having the formula I, with a chain length of at least 50 and at most 1000 units,

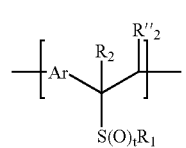

(I)

in which formula I:
t is equal to 0, 1, or 2,
$R_1$ is chosen from the group comprising a non-branched $C_1$-$C_{20}$-alkyl group, a branched $C_3$-$C_{20}$-alkyl group, a cyclic $C_4$-$C_{20}$-alkyl group, a $C_1$-$C_4$-alkyl-substituted cyclic $C_4$-$C_{20}$-alkyl group, a phenyl group, and a benzyl group, which groups may comprise heteroatoms, and
$R_2$, $R'_2$ and Ar are identical to $R_2$, $R'_2$, and Ar, respectively, in formula VI.

The electronic device according to the invention has a number of advantages thanks to the use of polymers with chain lengths between 50 and 1000, in which the Ar group comprises an aromatic system of 4 to 6 carbon atoms and possibly a heteroatom, and is possibly substituted. The polymers were found to have fewer defects. As a result, the polymer has better properties. The use of the polymer with a shorter chain length furthermore reduces the cost price of the device; not only is the method of preparing the precursor polymer easier than the known method, but the prepared solution of the precursor polymer also has a lower viscosity and is thus easier and faster in processing.

In a first embodiment, the device according to the invention is a light-emitting diode in which —Ar— is equal to the unit having the formula V. Light-emitting diodes manufactured partly from polymeric material are important elements in the development of displays.

In a second embodiment, the device according to the invention is an integrated circuit in which —Ar— is equal to the unit having the formula IV. Integrated circuits which are at least partly manufactured from polymeric material have the advantages of a low cost price and a high flexibility. They are highly suitable for use in transponders for the identification of items. Such circuits may in principle also be integrated with light-emitting diodes.

These and other aspects of the method of preparing a polymer with structural units having the formula I, the method of preparing a compound having the formula VII, the method of manufacturing an electronic device, and compounds having the formula II and polymers comprising structural units having the formula III and I according to the invention will now be described in more detail with reference to drawings and embodiments, in which.

Figure 1:
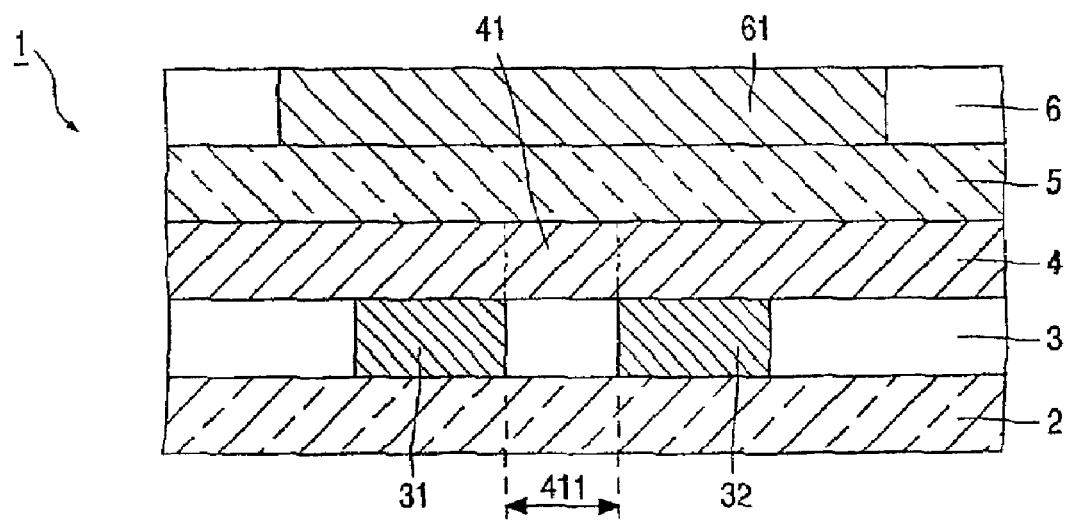
FIG. 1 is a diagrammatic cross-sectional view of a transistor.

The transistor 1 depicted in FIG. 1 comprises an electrically insulating substrate 2, a first layer 3 thereon of a polymeric material, for example polyaniline, comprising electrically conductive portions and offering space to a source electrode 31 and a drain electrode 32. The electrically non-conductive portions of the first layer 3 may be removed. The organic semiconductor layer 4 comprising polythienylene-vinylene prepared by the method according to the invention has a channel 41 whose channel length is referenced 411. An electrically insulating layer 5, for example made of polyvinylphenol, covers the layer 4 and insulates the gate electrode 61 from the channel 41. The gate electrode forms part of a second conductive layer 6 which is manufactured, for example, from doped polyaniline. The electrically non-conductive portions of this second conductive layer may be removed.

Other examples of field effect transistors comprise bottom-gate structures and transistors with alternative organic polymers or non-polymeric layers for the insulating and conducting portions. The transistor may form part of a wider circuit, such as an inverter, an oscillator, or an integrated circuit. It is possible to manufacture not only a field effect transistor, but also a bipolar transistor with a semiconductor layer of polythienylene-vinylene by the method according to the invention.

Figure 2:
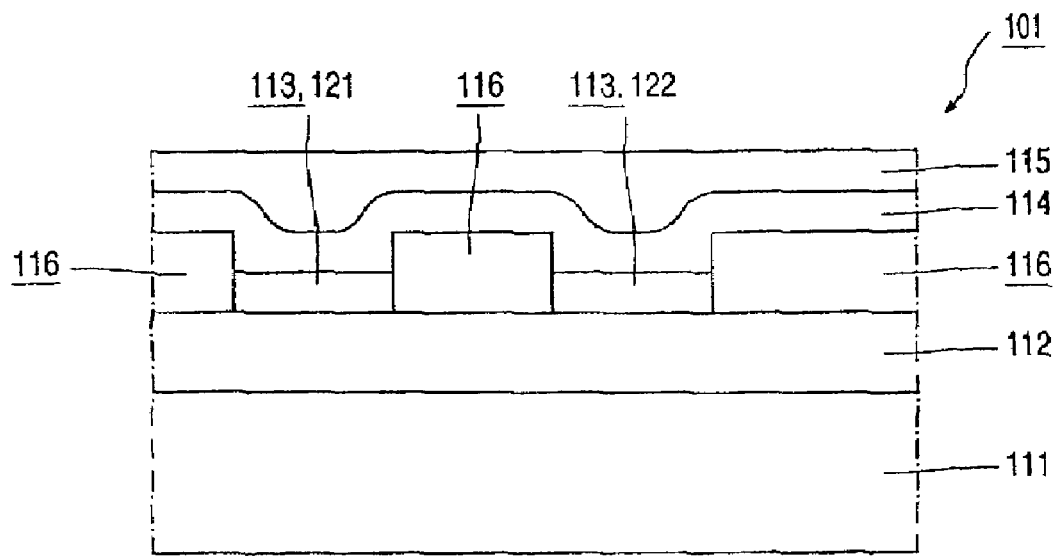
FIG. 2 is a diagrammatic cross-sectional view of a light-emitting diode.

FIG. 2 diagrammatically shows a cross-section through a light-emitting diode 101. This electronic device comprises a substrate 111, a first electrode layer 112, a first relief structure 113, an electroluminescent layer 114, and a second electrode layer 115. The substrate 111 comprises glass, the first electrode layer comprises ITO, and the second electrode layer comprises Al. The first relief structure 113 comprises electrically conductive poly(3,4-ethylenedioxy)-thiophene, (PEDOT), and the electroluminescent layer 114 comprises polyphenylene-vinylene. The patterns 121, 122 have a dimension of 100 μm in length and width. The relief structure 113 and the electroluminescent layer 114 each have a thickness of the order of 100 nm. The light-emitting diode is manufactured through sputtering of ITO onto the substrate 111. A solution of polyvinylphenol and the cross-linking agent hexamethoxymethylmelamine (HMMM) in propyleneglycolmethylether acetate is spin-coated onto the ITO, whereby a layer of 200 nm is formed. The layer is exposed in accordance with a chosen pattern and washed, such that a patterned layer 116 is formed. The polyvinylphenol is removed in those regions where the patterns 121, 122 are to be formed. An aqueous colloidal solution of PEDOT, poly (styrenesulfonic acid), and a photo-initiator is provided on the substrate by means of spin coating, so that a layer is formed. The layer is exposed in accordance with a desired pattern and developed in water, so that the relief structure 113 is created. Then the oxidized precursor polymer of polyparaphenylenevinylene is provided as the layer 114. This precursor polymer comprises structural units having the formula I, in which Ar is equal to benzyl, and t is equal to 1. The sulfoxy group is eliminated by heating, and a layer of polyparaphenylenevinylene is formed. Finally, the second electrode layer is provided by means of sputtering.

EMBODIMENT 1

Preparation of 2,5-bis(phenylthiomethyl)thiophene, the Compound having the Formula II with Ar Equal to Thienylene—the Unit having the Formula IV with X Equal to S, $R_3$, $R'_3$ Equal to H—, $R_2$ and $R'_2$ Equal to H, and $R_1$ and $R_1'$ Equal to Phenyl.

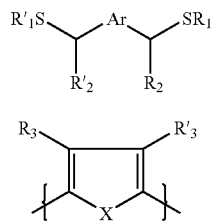

(II)

(IV)

A mixture of paraformaldehyde (45 g) and 30% hydrochloric acid (200 ml) is heated for 90 minutes at 60° C. The solution thus formed is cooled down, whereupon a mixture of thiophenol (156 ml) and thiophene (57 ml) is added in 20 minutes at 30-35° C. The mixture is heated at 70-75° C. for three days under mechanical stirring and subsequently poured into a mixture of toluene and water. After the layers have separated and the organic layer has been washed with water, the organic layer is filtered through Celite and washed with ammonia. While stirring, the toluene is evaporated. The solid residue is filtered through 200 g silica gel, for which a mixture of hexane and some ethyl acetate is used as the eluent. The resulting effluent is evaporated, so that a residue remains. This is recrystallized from a mixture of hexane and ethyl acetate. The filtrate is given an aftertreatment. The total yield is 108.0 g (46%, based on thiophene).

EMBODIMENT 2

Preparation of 2,5-bis(butylthiomethyl)thiophene, the Compound having the Formula II with Ar Equal to Thienylene, $R_2$ and $R_2'$ Equal to H, and $R_1$ and $R_1'$ Equal to Butyl.

250 ml 33% sodium hydroxide solution is slowly added to a mixture of butanethiole (157 ml), 2,5-bischloromethylthiophene (138 g), 250 ml toluene, and 2.0 g benzyltriethylammonium chloride. The temperature of the reaction mixture gradually rises to 60° C. during this, for which some cooling is necessary. The mixture is stirred for 4 hours at 60° C., whereupon it is cooled down. The organic and the watery layer in the mixture are separated, and the organic layer is washed with 2×250 ml water. Then the organic layer is evaporated, so that a residue remains. This residue is purified by means of Kugelrohr distillation. The first fraction obtained is 22 g monobutylthiomethylthiophene, the second fraction is the desired product (134 g, 33% yield based on butanethiole).

EMBODIMENT 3

Polymerization of 2,5-bis(phenylthiomethyl)thiophene into the Polymer with Structural Units having the Formula I in which Ar is Equal to Thienylene, $R_2$ and $R_2"$ are Equal to H, $R_1$ is Equal to Phenyl, and t is Equal to 0.

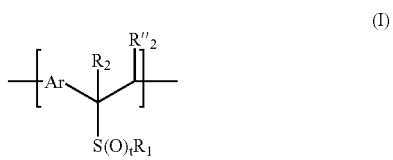

(I)

A solution of lithium diisopropylamine is prepared in that 30 ml 2.4 N butyllithium in hexane is added to diisopropylamine (8.0 g) in 75 ml THF at −30° C. This solution is stirred for 15 minutes. Then it is cooled down to −70° C. At this temperature, a solution of 2,5-bis(phenylthiomethyl)thiophene (22 g) in 225 ml THF is added. The dark solution is heated to 0° C. over a period of three hours. After the addition of 100 ml water, the watery and the organic layers are separated, and the organic layer is washed with another 100 ml water. The solution is partly evaporated, and the residue (c. 100 ml) is slowly added to 200 ml methanol under thorough stirring. The supernatant substance is decanted from the viscous oil, which oil is washed with a little methanol. Drying of the viscous oil in high vacuum yields the polymer mentioned above in the form of a foam. $^1$H-NMR (CDCl$_3$): δ3.2 (bm, 2H), 4.4 (bt, 1H), 6.3 (bs, 2H), 7.0-7.3 (m, 5H). Small signals are observed at 4.1 CH$_2$SPh end groups) and 6.5 (bs).

EMBODIMENT 4

Alternative Polymerisation of 2,5-bis(phenylthiomethyl)thiophene into the Polymer with Structural Units having the Formula I in which Ar is Equal to Thienylene, $R_2$ and $R_2"$ are Equal to H, $R_1$ is Equal to Phenyl, and t is Equal to 0.

A solution of 2,5-bis(phenylthiomethyl)thiophene (6,57 g, 20 mmole) and tetramethylethylenediamine (2,91 g, 25 mmole) in dry TBF (40 g) was cooled to −40° C. A 1.6 M solution of n-butyllithium in hexane (15.6 mL, 25 mmole) was added. The reaction mixture was warmed to −10° C. in 1.5 hours and quenched by adding 50 mL of water, giving organic fractions and an aqueous fraction. The aqueous fraction was extracted with 2×50 mL of CH$_2$Cl$_2$. The combined organic fractions were washed with water (100 mL), aqeous 1 M HCl solution (2×101 mL), water (100 mL), dried over MgSO$_4$ and precipitated in methanol (500 g). This sequence was repeated three times to afford a yellow-brown polymer after drying in vacuo.

EMBODIMENT 5

Polymerization of 2,5-bis(butylthiomethyl)thiophene into the Polymer with Structural Units having the Formula I in which Ar is Equal to Thienylene—the Unit having the Formula IV with X Equal to S, $R_3$, $R_3'$ Equal to H—, $R_2$ and $R_2"$ Equal to H, $R_1$ Equal to Butyl, and t Equal to 0.

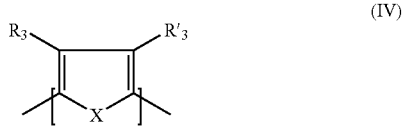

(IV)

A solution of lithium diisopropylamine is prepared in that 30 ml 2.4 N butyllithium in hexane is added to diisopropylamine (8.0 g) in 75 ml THF at −30° C. This solution is stirred for 15 minutes. It is then cooled down to −70° C. At this temperature, a solution of bis(butylthiomethyl) thiophene (17 g) in 100 ml THF is added over a few minutes. The dark solution is heated to 0° C. over a period of 2 hours. Then the solution is put in ice and stirred for 3 hours at 0° C. 2 ml methanol is added to the mixture, and then water is added. The product is extracted with toluene. Washing with water and evaporation yields the polymer in the form of a viscous oil, said polymer comprising units having the formula I in which Ar is thienylene, $R_2$ and $R_2''$ are equal to H, $R_1$ is equal to butyl, and t is equal to 0. $^1$H-NMR (CDCl3): δ0.8 (m, 3H), 1.2-1.6 (m, 4H), 2.3 (m, 2H), 3.2 (bm, 2H), 4.1 (bt, 1H), 6.4 (bs, 1H), 6.5 (bs, 1H). Small signals are observed at 3.8 (bs, $CH_2SBu$ end groups) and 6.65 (bs).

EMBODIMENT 6

Oxidation of the Polymer with Structural Units having the Formula I in which Ar is Equal to Thienylene, $R_2$ and $R_2''$ are Equal to H, $R_1$ is Equal to Butyl, and t is Equal to 0 into a Polymer having Such Structural Units in which t is Equal to 1.

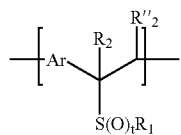

(I)

The polymer prepared from 2,5-bis(phenylthiomethyl) thiophene (9.0 g, 27.4 mmole) is dissolved in 150 ml dichloromethane. While the solution is cooled down to a temperature of between −15 and −20° C., m-chloroperbenzoic acid (70-75%, 6.30 g, max. 27.4 mmole) is added in portions over a period of 10 minutes. A mixture is created thereby which is stirred for one hour, during which the temperature is allowed to rise to 5° C. Then the mixture is poured into 500 ml methanol under thorough stirring. This mixture is further processed. The result is 3.82 g oxidized polymer.

EMBODIMENT 7

Polymerization of 2,5-bis(phenylthiomethyl)-1,1'-biphenyl, the Compound having the Formula II in which Ar is Equal to 1,1'-biphenylene—the Unit having the Formula V with $R_5$ Equal to Phenyl, $R_5'$, $R_5''$ Equal to H—, $R_1$ and $R_1'$ Equal to Phenyl, and $R_2'$ Equal to H.

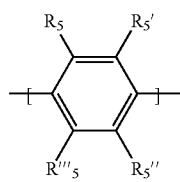

(V)

A solution of lithium diisopropylamine is prepared from diisopropylamine (5.25 g, 52.0 mmole), n-hexyllithium in hexane (18.0 ml of a 2.4 N solution, 43.2 mmole), and 50 ml tetrahydrofurane in a conventional manner. A solution of 2,5-bisphenylthiomethyl-1,1'-biphenyl (15.83 g, 39.8 mmole) in 100 ml tetrahydrofurane is added to this solution at a temperature lower than −60° C. over a period of 10 to 15 minutes. The solution is heated to −10° C. in 90 minutes and is then stirred at −5 to −10° C. for another 90 minutes. Water (100 ml) is added, which gives rise to a two-phase system of an aqueous layer and an organic layer. The layers are separated and the organic layer is washed with 100 ml water. Then the solvent is evaporated from the organic layer, so that the polymer remains. The polymer comprises structural units having the formula I in which Ar is equal to 1,1'-biphenylene, $R_1$ is equal to phenyl, $R_2$ and $R_2''$ are equal to H, and t is equal to 0.

EMBODIMENT 8

Direct Elimination of —$SR_1$-group from a Precursor Polymer of polyphenylene-vinylene by Heating Under Catalysis of Acid To a solution of 100 mg phenylsulfide precursor of poly-3-(4-(3,7-dimethyloctyloxy)phenyl)-1,4-phenylenevinylene in 10 ml toluene 0,005 grams of p-toluenesulfonic acid is added. The solution is refluxed during 4 hours in a nitrogen atmosphere. In this 4-hour period, the solution turns red and fluorescent. GPC chromatography is done, after 1 hour, in order to test the precursor polymer and the resulting polymer. The precursor shows a main peak at 220 nm with an intensity=0.5 AU and a second peak at 303 nm with an intensity of 0.15 AU. The resulting polymer shows a first peak at 230 nm at an intensity of 0.28 AU, a second peak at 303 nm with an intensity of 0.14 AU and a third peak at 446 nm with an intensity of 0.18 AU. This results show that a conjugated system has been formed by elimination of the phenyl sulfide group. The precursor polymer has a number average molecular weight $M_n$ of 13,000 g/mole and a weight average molecular weight $M_w$ of 24,000 g/mole. The resulting polymer has a $M_n$ of 16,000 g/mole and an $M_w$ of 29,000 g/mole.

EMBODIMENT 9

Second Example of Direct Elimation of —$SR_1$-group

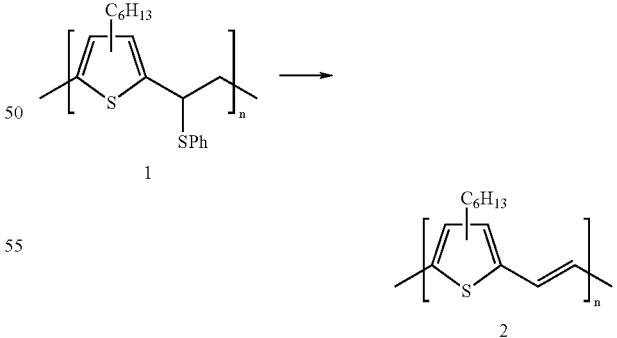

A degassed solution of 1 (0.91 g, 3 mmoles) and p-toluenesulfonic acid (28.5 mg, 0.15 mmoles) in toluene (75 mL) was heated under reflux for two hours. The resulting deep-blue solution was cooled to room temperature and concentrated in vacuo. The crude material was dissolved in THF and precipitated in methanol. This procedure was repeated two times.

EMBODIMENT 10

Third Example of Direct Elimation of —SR$_1$-group

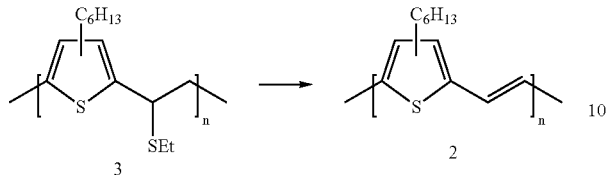

A degassed solution of 1 (0.76 g, 3 mmoles) and p-toluenesulfonic acid (28.5 mg, 0.15 mmoles) in toluene (75 mL) was heated under reflux for two hours. The resulting deep-blue solution was cooled to room temperature and washed with aqueous 0.5 M NaHCO$_3$ (2×30 mL) and demineralised water (2×30 mL). The organic fraction was concentrated in vacuo. The crude material was dissolved in THF and precipitated in methanol. This procedure was repeated two times.

EMBODIMENT 11

Fourth Example of Direct Elimination of SR$_1$-group

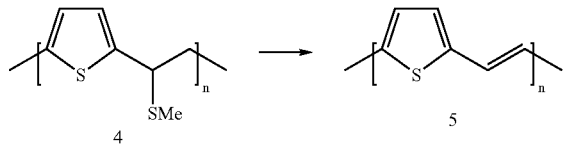

The precursor polymer 4 was spincoated from a 0.5 weight % chloroform solution onto a regular MISFET test substrate. The precursor polymer 4 was converted into 5 by annealing the substrate at 180° C. in a nitrogen/HCl atmosphere (partial HCl pressure: 10$^{-3}$ bar) for 45 min. After the conversion, the substrate was allowed to cool to room temperature in a flow of pure nitrogen in order to remove traces of acid.

What is claimed is:

1. A method of preparing a polymer which comprises structural units of formula I,

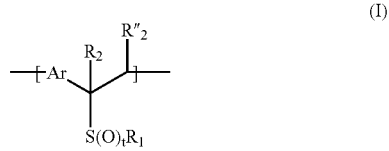

in which formula:
  Ar is an aromatic cyclic system with 4 to 20 carbon atoms, which may be substituted with a substituent chosen from the group consisting of a non-branched C$_1$-C$_{20}$-alkyl, a C$_3$-C$_{20}$-alkoxy, a C$_1$-C$_{20}$-alkylsulfate, a branched C$_3$-C$_{20}$-alkyl, a phenyl group and a benzyl group and which may comprise up to 4 heteroatoms chosen from the group consisting of oxygen, sulfur and nitrogen in the aromatic cyclic system,
  t is equal to 0, 1 or 2,
  R$_1$ is chosen from the group consisting of a non-branched C$_1$-C$_{20}$-alkyl group, a branched C$_3$-C$_{20}$ alkyl group, a cyclic C$_4$-C$_{20}$-alkyl group, a C$_1$-C$_4$-alkyl-substituted cyclic C$_4$-C$_{20}$-alkyl group, a phenyl group and a benzyl group, which groups may comprise heteroatoms,
  R$_2$ and R"$_2$ are each chosen for the group consisting of a hydrogen atom, a C$_1$-C$_{20}$-alkyl group, and a C$_4$-C$_{20}$-aryl group, which groups may comprise substituents, characterized in that the method starts with a compound having the formula II

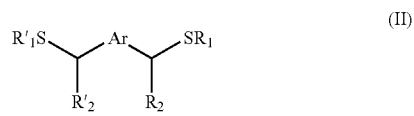

in which formula
  R'$_1$ is chosen from the group consisting of a non-branched C$_1$-C$_{20}$-alkyl group, a branched C$_3$-C$_{20}$-alkyl group, a cyclic alkyl group, a C$_1$-C$_4$-alkyl-substituted cyclic alkyl group, a phenyl group, and a benzyl group, which groups may comprise heteroatoms,
  R$_1$, R$_2$ and Ar are equal to R$_1$, R$_2$ and Ar in formula I, and
  R'$_2$ is chosen from the group consisting of a hydrogen atom, a C$_1$-C$_{20}$-alkyl group, an a C$_4$-C$_{20}$-aryl group, which groups may comprise substituents,
and that the polymer with structural units of the formula I is prepared through polymerization with the aid of a base into a polymer which comprises units having the formula III

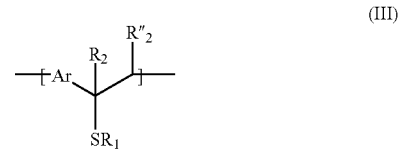

in which formula
  R$_1$, R$_2$ and Ar are equal to R$_1$, R$_2$ and Ar in formula II, and
  R"2 is chosen from the group comprising R$_2$ and R'$_2$,
and for the preparation of the polymer with units having the formula I, in which formula t is equal to 1 or 2, through oxidation of at least a number of the units of the polymer having the formula III.

2. A method as claimed in claim 1, characterized in that the method starts with a compound having the formula II in which —Ar— is the unit having the formula IV

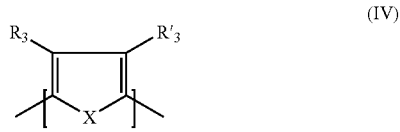

in which formula
  X is chosen from the group consisting of O, S, NR$_6$,
  R$_2$ and R'$_3$ are chosen from the group consisting of a hydrogen atom, a chlorine atom, a bromine atom, a fluorine atom, and an iodine atom, a $C_1$-$C_4$-alkyl group, a carbonitryl group, a trihalomethyl group, a hydroxy group, a nitro group, an amino group, a carboxyl group, a sulfoxyl group, a sulfonate group, a carbonate group, a substituted and non-substituted phenyl group, an alkylaryl group, an alkalkyl group, an alkoxy group, and a thioalkoxy group, and $R_6$ is chosen from the group consisting of a hydrogen atom, a $C_1$-$C_{20}$-alkyl group, an aryl group, a $C_1$-$C_{20}$-alkylaryl group and an arylalkyl group.

3. A method as claimed in claim 1, characterized in that the method starts with a compound having the formula II in which —Ar— is the unit having the formula V

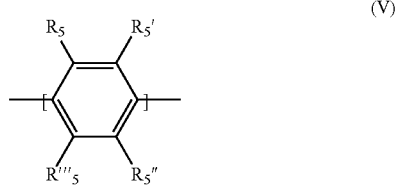

in which formula $R_5$, $R'_5$, $R''_5$ and $R'''_5$ are chosen from the group consisting of a hydrogen atom, a chlorine atom, a bromine atom, a fluorine atom, an iodine atom, a $C_1$-$C_{22}$-alkyl group, a carbonitryl group, a trihalomethyl group, a hydroxy group, a nitro group, an amino group, a carboxyl group, a sulfoxyl group, a sulfonate group, a carbonitrate group, an optionally substituted phenyl group, a $C_1$-$C_{22}$-alkylaryl group, a $C_1$-$C_{22}$-arylalkyl group, a $C_1$-$C_{22}$-alkoxy group, and a $C_1$-$C_{22}$-thioalkoxy group.

4. A composition of polymers with structural units having the formula IX:

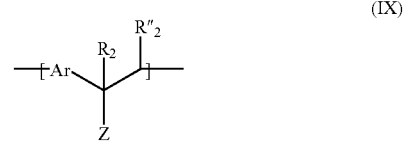

Ar is an aromatic cyclic system with 4 to 20 carbon atoms, which may be substituted with a substituent chosen from the group consisting of a non-branched $C_1$-$C_{20}$-alkyl, group, a $C_3$-$C_{20}$-alkoxy group, a $C_1$-$C_{20}$-alkyl-sulfate group, a branched $C_3$-$C_{20}$-alkyl group, a phenyl group and a benzyl group and which may comprise up to 4 heteroatoms chosen from the group consisting of oxygen, sulfur and nitrogen in the aromatic cyclic system, $R_2$ and $R_2'$ are chosen from the group consisting of a hydrogen atom and $C_1$-$C_{20}$-alkyl and a $C_4$-$C_{20}$-aryl group, which groups may comprise substituents, and Z is chosen from a group consisting of $S(O)pR_1$, $OR_2$, in which p is equal to 0, 1 or 2, and $R_1$ and $R_2$ are chosen from the group comprising a non-branched $C_1$-$C_{20}$-alkyl group, a branched $C_3$-$C_{20}$ alkyl group, a cyclic $C_4$-$C_{20}$ alkyl group, a $C_1$-$C_4$-alkyl-substituted cyclic $C_4$-$C_{20}$-alkyl group, a phenyl group, and a benzyl group, which groups may contain heteroatoms, wherein a first fraction of the composition comprises polymers with structural units having the formula IX with Z equal to $S(O)pR_1$ and a chain length of 50 to 1000 units, and a second fraction of the composition comprises polymers with a chain length of more than 1000 units.

* * * * *